United States Patent [19]
Hansen et al.

[11] Patent Number: 5,687,550
[45] Date of Patent: Nov. 18, 1997

[54] BLOW MOLDING SEALED CONTAINER SYSTEM

[75] Inventors: Bernd Hansen, Heerstrasse 16, D-74429 Sulzbach-Laufen, Germany; Willy Leu, Mosli, Switzerland

[73] Assignee: Bernd Hansen, Sulzbach-Laufen, Germany

[21] Appl. No.: 551,025

[22] Filed: Oct. 31, 1995

[30] Foreign Application Priority Data

Nov. 3, 1994 [DE] Germany ............ 44 39 231.1

[51] Int. Cl.⁶ .................................... B65B 47/08
[52] U.S. Cl. .................. 53/453; 53/452; 53/140; 53/469; 53/479
[58] Field of Search .............. 53/140, 453, 467, 53/469, 452; 264/524, 529, 526; 425/524, 525

[56] References Cited

U.S. PATENT DOCUMENTS

| | | | |
|---|---|---|---|
| 3,464,085 | 9/1969 | Burkett et al. | 53/140 |
| 3,523,330 | 8/1970 | Gallay | 53/140 |
| 4,688,369 | 8/1987 | Cornish et al. | 53/467 X |
| 4,707,966 | 11/1987 | Weiler et al. | 53/140 X |
| 4,790,117 | 12/1988 | Hansen | 53/140 X |
| 4,905,450 | 3/1990 | Hansen et al. | 53/453 X |
| 5,351,462 | 10/1994 | Anderson et al. | 53/140 X |

FOREIGN PATENT DOCUMENTS 653607  1/1986  Switzerland.

*Primary Examiner*—Linda Johnson
*Attorney, Agent, or Firm*—Roylance,Abrams,Berdo & Goodman,L.L.P.

[57] ABSTRACT

A blow molding method manufactures a sealed container and fills the container with a substance. The container body is connected to a head or top. A part of the head can be detached for opening of the container. A segment of an extruded tube is mounted in a blow mold having an axially movable mold base. The diameter of the extruded tube is slightly greater than the diameter of the head or top. Following the closing of the tube end forming the bottom of the container, air is blown into the tube and simultaneously the mold base is moved toward the top jaws of the blow mold forming the head. After filling of the container and possibly mounting of an insert body into the top segment of the tube forming the container head or top, the mold base is moved still further in the direction of the top jaws, until the container is free of air. Then, the head is formed and is sealed securely with the outer surface of the insert body.

8 Claims, 2 Drawing Sheets

5,687,550

BLOW MOLDING SEALED CONTAINER SYSTEM

FIELD OF THE INVENTION

The present invention relates to a blow molding method for the sterile manufacture of a sealed container filled with a substance. The container has a body, a detachably mounted head to facilitate opening the container, and a transition part extending between the head and body in a substantially radial plane. The head has a diameter considerably smaller than that of the body. The present invention also relates to the container produced by this method.

BACKGROUND OF THE INVENTION

Known blow molding processes for producing containers cannot produce a container without oblique transition parts between the container body and head, where the diameter of the body is at least four times the diameter of the head or top and where the transition part has a wall thickness which is greater than the wall thickness of the side wall of the body.

SUMMARY OF THE INVENTION

An object of the present invention is to provide a blow molding method in which containers can be produced without oblique transition parts between the head and body, where the containers have a relatively large, preferably more than four times as large, size differential ratio of the body diameter to the head diameter. In other words, the ratio between the body diameter and the head or top diameter is at least four.

Another object of the present invention is to provide a blow molding method for producing containers having a greater wall thickness in the area of the transition part between the body and head than in the side wall of the body and having an insert body inserted in the head or top of the container.

A further object of the present invention is to provide a blow molding method for producing a container with complete filling of the body of the container which is air-free.

The foregoing objects are basically obtained by a method for manufacturing a sealed container filled with a liquid substance, comprising the steps of positioning a portion of an extruded tube in a blow mold to form a container having a body with a body diameter, a detachable head to facilitate opening the container, with a head diameter being considerably smaller than the body diameter, and a transition part between the body and the head substantially extending in a radial plane, the tube having a diameter slightly greater than the head diameter; closing bottom end of the tube forming a bottom of the container; blowing air into the tube, after the tube bottom end is closed, and simultaneously moving a mold base in a first movement toward top jaws of the blow mold, which top jaws form the container head; filling the container in the blow mold with the liquid substance; moving the mold base further toward the mold top jaws until the container is free of air; and forming the tube top segment into the container head and sealing the formed container.

With a considerable size differential ratio of the body and head diameters, the moving of the mold base up toward the mold top jaws during expansion or enlargement of the tube segment, while the tube segment is in the mold, produces a transition part free of inclination or tilt between head and body of the container. Additionally, the wall thickness in the area of the transition part between head and body can be even considerably greater than the wall thickness in the side wall of the body. Furthermore, as a result of the movement of the mold base in the direction of the head or top, following filling of the container, before closing of the top, the container will be completely free of air or at the most only contain only a negligible volume of air inside the insert body.

During its first step of movement, the mold base preferably is moved until it attains the position corresponding to the size of the container in sealed state. During the filling process the mold base is moved a short distance back or away from the container head. The container then contains a slight excess of filled-in substance. The excess substance can be expelled by a return movement of the mold base into the position corresponding to the size of the container in closed state to assure that the container in this state is filled quite completely and is air-free.

The plastic material used for the extrusion is run through a sterilization process. The container is blow-molded with sterile air and is filled with a sterile product. An insert body can be inserted antiseptically. The greatly improved sterility is thereby guaranteed to be reliable.

Instead of producing greater pressure inside the extruded tube upon its expansion, a vacuum pressure can be provided and exerted on the outside of the tube only, or in addition to the pressure inside.

In one preferred embodiment, during the first movement step of the mold base, the blow molding air is blown in only at low pressure. Shortly before the mold base reaches its end position, the air pressure is then increased to its highest level to guarantee complete fitting of the molded container against the end of the mold passage on the inside wall of the mold. This avoids unfavorably influencing the shaping process of the tube during expansion.

In an advantageous manner, the excess filled-in substance and the air still present in the container are removed by means of the movement of the mold base toward the head or top. Additionally and preferably, following the filling of the container and during movement of the mold base concomitant with the filling, the air and excess filled-in substance are suctioned out. Usually, an insert body has already been inserted into the head or top beforehand. Thus, this suction removal preferably occurs through the inserted body. If the insert body does not have a hollow needle extending through it, the insert body can be provided with a longitudinal channel.

Generally speaking the engaging pressure of the tube wall on the insert body is sufficient to produce a solid and tight connection. However, if necessary, the insert body can be welded together with the head or top around the surrounding periphery, for instance by means of ultrasound or a laser beam.

Yet other objects of the present invention are to provide a container manufactured according to the method of the present invention, where the container can be easily operated manually to discharge the filled-in substance in an axial or longitudinal direction.

The foregoing objects are basically obtained by a container formed by blow molding, comprising a body having a body side wall with a body wall diameter and a body wall thickness. The body is filled with a liquid substance. A head is detachably mounted on the body to facilitate opening the container. The head has a head diameter considerably smaller than the body diameter. A transition part between the body and the head substantially extends in a radial plane. The transition part has a transition part wall thickness. The body wall thickness is significantly smaller than the transition part wall thickness between the body and the head.

By virtue of the different wall thicknesses in the area of the head passage and the base relative to the side wall of the body, a sufficient bend resistance of the transition part and of the bottom can be achieved. The side wall of the body can still have good deformability. Thus, a container can be formed with a bottom which can be brought into direct contact with the transition part between head and body.

For reinforcement of the bottom part and the transition part between head or top and body, one part can have at least one indentation and the other part can have at least one projection directed into this indentation.

In one preferred embodiment, an insert body is mounted in the container head, and is subdivided or subdividable in transverse direction. The division point or plane lies in the area of a break point or line in the top or head part. In this manner, the insert body is separated upon opening the container by tearing off a part of the top or head. Preferably, form-locking connections are provided in axial alignment between the insert body and the head to ensure that the two parts of the insert body remain incorporated with the respective parts of the top surrounding them during opening.

The insert body, for example, can incorporate a hollow needle securely mounted in that part of the insert body mounted in the part of the head which is undetachable from the body. The hollow needle projects into a longitudinal channel of the other part of the insert body. During opening of the container, this hollow needle is freed or exposed along the needle length extending within the removable part of the insert body bearing the needle. During the manufacturing procedure, air and excess filler material can be suctioned out through this hollow needle.

To further facilitate application of the force required to open the container, a grip or handle part is constructed preferably at that part of the top which covers the end of the insert body remote from the body. The grip or handle advantageously stands away from the top in longitudinal or axial alignment with the top or head.

Other objects, advantages and salient features of the present invention will become apparent from the following detailed description, which, taken in conjunction with the annexed drawings, discloses a preferred embodiment of the present invention.

BRIEF DESCRIPTION OF THE DRAWINGS

Referring to the drawings which form a part of this disclosure.

DETAILED DESCRIPTION OF THE INVENTION

A container 1 can be characterized as an ampule on account of its small volume. The container comprises an essentially cylindrical body 2. The body axial length is considerably smaller than its diameter. A head or top part 3 is attached coaxially to the front end of body 2, opposite the body bottom 4. The outside diameter of body 2 is approximately four times the dimensions of the outside diameter of head or top part 3.

Figure 1:
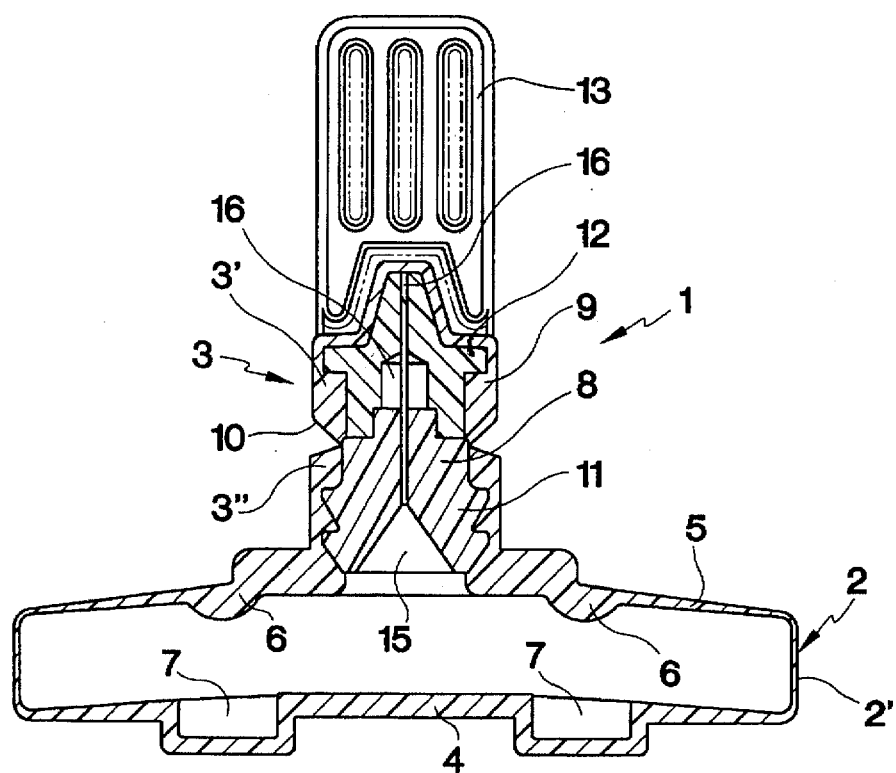
FIG. 1 is a side elevational view in section of a finished container.

As shown in FIG. 1, the transition part 5 extending from body cylindrical side wall 2' to head 3 is practically free of tilt or incline. In other words, transition part 5 lies almost in a radial plane. As FIG. 1 further shows, the inner annular area of transition part 5 attached directly to the head is of relatively great thickness. From this inner annular zone outward, the thickness of transition part 5 diminishes continuously toward side wall 2' until it reaches a thickness equal to the thickness of side wall 2'. However, the thickening of the inner annular zone can be eliminated and the thickness of transition part 5 can decrease from head or top 3 radially outward without stages to side wall 2'.

On the transition part from the inner annular zone to the outer radial area of transition part 5, an annular bead 6 is constructed on the inside surface projecting downward toward body bottom 4, and is concentric with head or top part 3. This bead is aligned with an annular groove 7 in bottom 4. The groove is open toward the bead. The wall thickness within annular groove 7 is constant and at least half the thickness of the annular zone of transition part 5. The material part limiting annular groove 7 extends outward over bottom 4. Outside annular groove 7, the wall thickness of bottom 4 diminishes toward wall 2' continuously until it reaches the wall thickness of the cylindrical wall.

Figure 2:
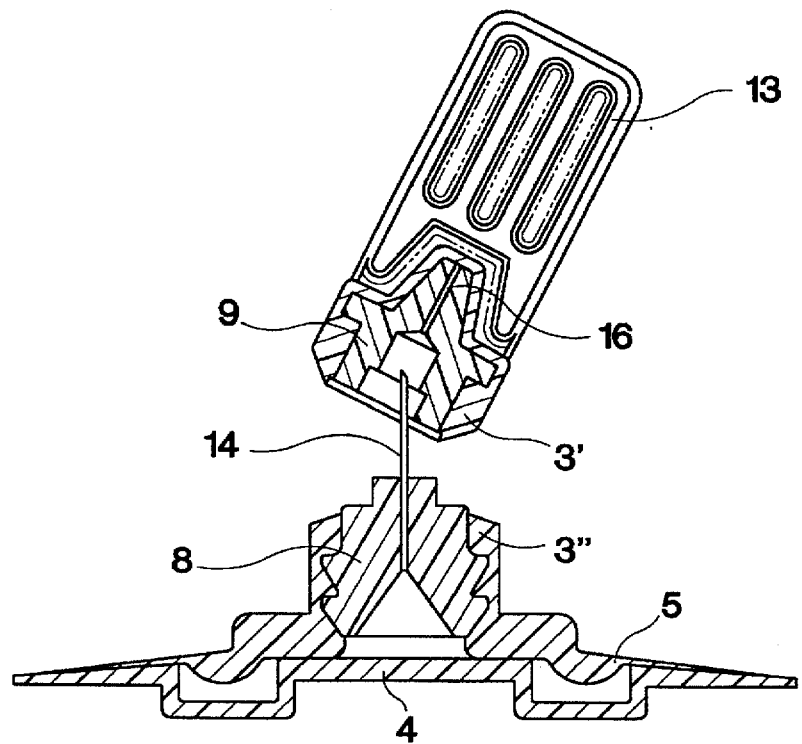
FIG. 2 is a side elevational view in section of the container of FIG. 1 after opening and reducing the volume.

By virtue of the relatively great thickness, as well as the stiffening generated by annular bead 6 and annular groove 7, transition part 5 and bottom 4 are so resistant to bending that the force required for deformation of wall 2' leads to no noticeable deformation of transition part 5 and bottom 4. Bottom 4, as shown in FIG. 2, can be brought into a collapsed position in contact with transition part 5. In the collapsed position, annular bead 6 projects into and fits in annular groove 7.

An insert body is mounted in top 3. The insert body is made of the same plastic as body 2 and top 3. Preferably, however, the insert body is of greater hardness than the plastic material forming body 2 and head or top 3. In the exemplary embodiment, the insert body comprises a first part 8 projecting into the thick annular zone of transition part 5, and a second part 9 mounted coaxial to first part 8 and spaced by a greater distance from the inside chamber of body 2. Second part 9 is mounted on a journal-like extension of first part 8. Second part 9 can also be configured in one integral piece with first part 8, and can have a break point or line between the two parts.

Top 3 is provided with such a break point, which in this case is approximately at the level of the dividing plane between first part 8 and second part 9 in the form of a circumscribing groove 10. Groove 10 penetrates radially from the outside and reduces the otherwise relatively considerable wall thickness of top 3 to a minimum. Circumscribing groove 10 has a triangular cross-sectional profile, to permit tilting of the part of top 3 to be broken off for the purpose of separating the parts.

A flange or, as shown, an annular sawtooth profile presenting teeth 11 are provided on the outside surface of first part 8 of the insert body. Teeth 11 engage the material forming top 3 and provide a form-locking connection in axial alignment between first part 8 and head or top 3. A corresponding connection between second part 9 and the removable part of head or top 3 is provided by a radially outward projecting flange 12 which is surrounded by the material of top 3.

On the end of top 3 further remote from body 2, a handle 13 is constructed. Handle 13 projects in axial alignment with the remainder of the top. By handle 13, top segment 3' of top 3 can be tipped away from bottom segment 3" of top 3 for opening of container 1. The handle is tipped until a tear occurs at the break point located at the bottom of the surrounding groove 10.

In the illustrated embodiment, a hollow needle 14 is affixed in the longitudinal axis of first part 8 of the insert body. The first part end turned or facing toward bottom 4 has a funnel 15 aligned with the first part longitudinal axis. A segment of hollow needle 14 extends and projects beyond the end of first part 8 of the insert body remote from bottom 4, as shown in FIG. 1.

Before opening the container, the needle extends into a central passage channel 16 in second part 9 of the insert body. Adjacent first part 8, central passage channel passage 16 has a considerably greater diameter than the diameter of hollow needle 14. The remainder of the central passage through second part 9 is of dimensions adapted to or substantially equal to the diameter of hollow needle 14. The end of central passage channel 16 remote from first part 8 is closed and sealed off by the material of top 3 which also forms a sheathing for the insert body.

Figure 3:
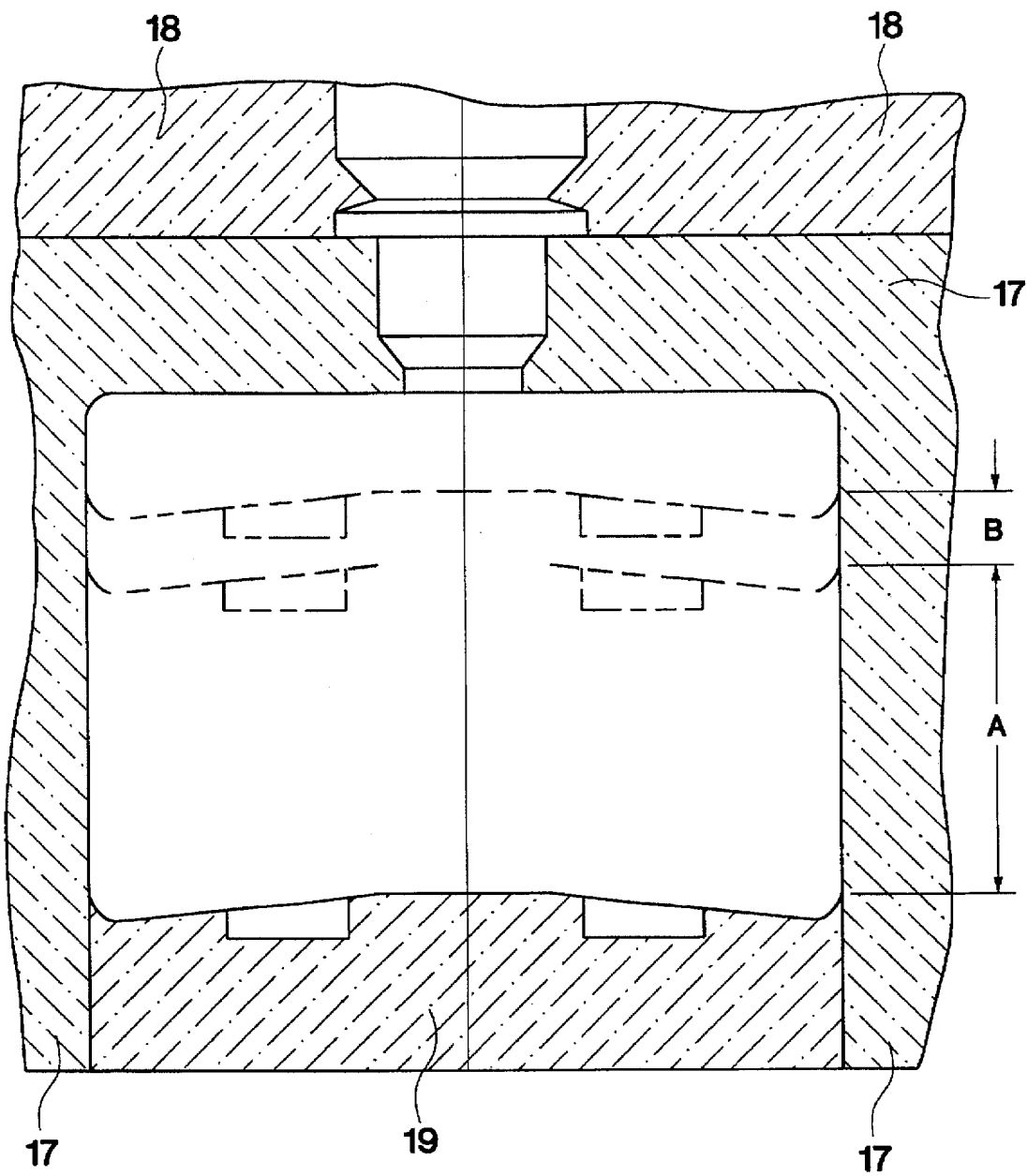
FIG. 3 is a partial, side elevational view in section diagrammatically illustrating the blow mold for forming the container of FIG. 1.

Container 1, as described above, is produced by a blow molding method from an extruded tube segment. As illustrated in FIG. 3, in addition to the main jaws 17 forming the body 2, this mold also has top jaws 18 and a segmented mold base 19. Mold base 19 can be moved axially, in other words back and forth, relative to top jaws 18, toward and away from the top jaws, and within main jaws 17. The segmented portions of the mold base can also be moved laterally or radially in the same manner as mold jaws 17 and 18.

After the extruded tube or parison, which is somewhat larger in diameter than the diameter of head or top 3, has been fitted in the mold, the tube is closed at its bottom end by closing the segmented portions of mold base 19. Mold base 19 is, at this time, located at the greatest possible distance from top jaws 18, as shown in FIG. 3. In the closed mold the blow molding process now begins. For this purpose, a blowing and filling taper plug is introduced into the top segment of the tube which will form top 3.

First, discharged air at greatly decreased pressure exits the taper plug and enters the tube. At the same time mold base 19 moves axially from the position of greatest distance from top jaws 18 into the position of least distance therefrom. Mold base 19 thus executes a total stroke, including partial strokes A and B, to an end position corresponding to the final size of the container. Shortly before mold base 19 reaches the end position, the pressure of the air is increased to standard. When the end position has been reached, the air feed is cut off and the filling process is begun. For the filling process, mold base 19 is drawn back to a distance corresponding to partial stroke B.

After the filling is completed and the blowing and filling taper plug has been removed from the mold, the insert body made up of a combination of the two parts 8 and 9 is inserted by means of a support into the top segment of the tube serving for formation of head or top 3. This segment of the tube is pressed by means of the top jaws against the outer surface of the insert body.

Furthermore, with the aid of the support, a vacuum force is exerted on the outwardly aligned portal opening of the central passage channel 16 of the insert body. Any air still present in the container and any excess filler material (e.g., a liquid substance) is suctioned out through passage channel 16. The removal of the air and excess filler material is aided by a movement of mold base 19 the distance of stroke B toward top jaws 18 into the position of smallest distance from top jaws 18. Subsequently, the handle is formed and top jaws 18 hermetically seal head or top 3 by welding the tube material with simultaneous formation of container handle 13.

Insofar as required, the wall forming head or top 3 can be welded with the insert bodies all the way around. For instance, the welding can be accomplished with the aid of a laser beam or with the aid of ultrasound.

When filler material is to be removed from container 1, top segment 3' of top 3 is broken away from bottom segment 3". Second part 9 of the insert body is then detached from the first part 8, whereupon hollow needle 14 is freed or exposed. If bottom 4 is pressed against transition part 5, the medium or contents are discharged from hollow needle 14 in drops or in a continuous stream.

While a particular embodiment has been chosen to illustrate the invention, it will be understood by those skilled in the art that various changes and modifications can be made therein without departing from the scope of the invention as defined in the appended claims.

What is claimed is:

1. A method for manufacturing a sealed container filled with a liquid substance, comprising the steps of:

positioning a portion of an extruded tube in a blow mold to form a container having a body with a body diameter, a detachably mounted head to facilitate opening the container with a head diameter considerably smaller than the body diameter and a transition part between the body and the head substantially extending in a radial plane, the tube having a diameter slightly greater than the head diameter, the blow mold including main laws between top jaws and a mold base;

closing a bottom end of the tube forming a bottom of the container;

blowing air into the tube, after the tube bottom end is closed, and simultaneously moving the mold base in a first movement toward the top jaws of the blow mold to decrease a space inside the main jaws;

filling the container in the blow mold with the liquid substance;

moving the mold base further toward the mold top jaws until the container is free of air; and forming a top segment of the tube with the top jaws into the container head and sealing the formed container.

2. A method according to claim 1 wherein the mold base first moves toward the mold top jaws to a first position corresponding to the size of the sealed container when air is blown into the tube; and the mold base moves slightly away from the mold top jaws during the filling of the container with the substance.

3. A method according to claim 2 wherein the mold base, after completion of the filling of the container with the substance, moves towards the mold top jaws back to the first position.

4. A method according to claim 1 wherein during the first movement of the mold base, air is first blown into the tube at a relatively low pressure; and shortly before the mold base reaches a first position corresponding to the size of the sealed container, the air pressure of the blown air is increased to a set value.

5. A method according to claim 3 wherein subsequent to filling the container with the substance, during movement of the mold base toward the mold top jaws and during the forming of the tube top segment to seal the container, air and any excess substance are removed from the container by suctioning.

6. A method according to claim 5 wherein an insert body is placed in the tube top segment before forming the container head, the tube top segment being formed to engage and seal peripheral surfaces of the insert body.

7. A method according to claim 6 wherein the suctioning of the air and the excess substance in the container occurs through the insert body.

8. A method according to claim 6 wherein the container head is welded about a periphery of the insert body.

* * * * *